United States Patent [19]

Knifton

[11] 4,260,820

[45] Apr. 7, 1981

[54] METHOD OF PREPARING ALIPHATIC CARBOXYLIC ACIDS

[75] Inventor: John F. Knifton, Austin, Tex.

[73] Assignee: Texaco Development Corp., White Plains, N.Y.

[21] Appl. No.: 77,970

[22] Filed: Sep. 24, 1979

[51] Int. Cl.$^3$ .............................................. C07C 51/12
[52] U.S. Cl. ..................... 562/517; 260/399; 260/404; 260/408; 260/413; 260/465.4; 560/265; 562/512; 562/519; 562/553; 562/577; 562/588; 562/590; 562/602; 562/605; 562/606; 562/607
[58] Field of Search ............... 562/517, 606, 577, 553, 562/590, 512, 602, 605, 588; 260/413, 408, 404, 465.4, 399

[56] References Cited

U.S. PATENT DOCUMENTS

| 2,534,018 | 12/1950 | Gresham et al. | 560/263 |
|---|---|---|---|
| 2,535,060 | 12/1950 | Gresham | 260/449 L |
| 2,549,470 | 4/1951 | Hawk | 260/449 L |
| 2,636,046 | 4/1953 | Gresham | 260/449 L |
| 3,285,948 | 11/1966 | Butler | 560/232 |

*Primary Examiner*—Vivian Garner
*Attorney, Agent, or Firm*—Carl G. Ries; Robert A. Kulason; James L. Bailey

[57] ABSTRACT

This invention pertains to the production of higher homologues of aliphatic carboxylic acids by reaction of said acids with carbon monoxide and hydrogen in the presence of one or more ruthenium catalyst components and an iodide or bromide promoter.

10 Claims, No Drawings

METHOD OF PREPARING ALIPHATIC CARBOXYLIC ACIDS

BACKGROUND OF THE INVENTION

1. Field of the Invention

This invention concerns a process for the preparation of carboxylic acids by synthesis gas homologation of aliphatic carboxylic acids by a specific catalyst system.

2. Description of the Prior Art

There is an ever increasing need for a wide variety of aliphatic carboxylic acids of differing carbon numbers and structures which have become important present articles of commerce. The many processes leading to the preparation of these acids include oxidation of saturated and unsaturated hydrocarbons, the carboxylation of mono-olefins, particularly α-olefins, and dienes such as conjugated dienes like 1,3-butadiene, and the carbonylation of lower aliphatic alcohols.

We now disclose a new preparative route to short-chain aliphatic acids involving the homologation of lower molecular weight aliphatic carboxylic acids. Homologation is effected by treatment of said carboxylic acids with synthesis gas (a mixture of carbon monoxide and hydrogen).

The homologation of carboxylic acids by means of synthesis gas has not, to our knowledge, been disclosed previously. The homologation of saturated alkyl, benzyl alcohols, and substituted benzyl alcohols, by synthesis gas to yield the corresponding higher molecular weight alcohols has been extensively studied. Pertinent examples include the homologation of methanol to ethanol, and the conversion of ethanol to propanol, butanol and pentanol isomers (see: "Carbon Monoxide in Organic Synthesis" by J. Falbe, pages 59-62 and I. Wender, Catal. Rev. Sci. Eng., 14, 97-129 (1976)). Cobalt carbonyls, with or without phosphine or metal modifiers, are commonly used as catalysts in such alcohol homologation reactions (see: L. N. Slaugh, Ger. Offn. No. 2,625,627 and P. D. Taylor, U.S. Pat. No. 4,111,837).

Related homogeneous cobalt carbonyl catalysts are also effective for the synthesis of aliphatic carboxylic acid via the carbonylation of the lower aliphatic alcohols. More recently, soluble rhodium catalysts have become the catalysts of ihorie in, for example, the synthesis of acetic acid via methanol carbonylation (Chem. Tech., p. 605, October 1971).

Other relevant homologation technology includes the recently reported homologation of dimethyl ether and methyl acetate to ethyl acetate (see: G. Braca et. al. 9, Amer. Chem. Soc., 100, 6238 (1978)).

It therefore becomes an object of the invention to provide a novel process of homologation of short-chain aliphatic carboxylic acids to the higher homologues thereof by means of a unique catalyst system. Said process involves the use of synthesis gas as the feedstock along with the acid which is homologized.

SUMMARY OF THE INVENTION

This invention comprises a novel process for preparing higher homologues of carboxylic acids by reaction of said acids with synthesis gas in the presence of one or more ruthenium-containing catalysts and a bromide or iodide promoter.

Said process is particularly characterized by the homologation of acetic acid to higher acids according to equation 1 which is illustrative of this process:

$$CH_3COOH + CO/H_2 \rightarrow C_nH_{2n+1}COOH \qquad (1)$$

Other lower aliphatic acids such as propionic acid and others containing 2-6 carbon atoms may also be homologized by a similar procedure.

DETAILED DESCRIPTION OF THE INVENTION

In brief, the process here involves preparing higher homologues of aliphatic carboxylic acids containing 2-6 carbon atoms which comprises the steps of contacting said aliphatic acid starting materials with at least a catalytic amount of a ruthenium-containing compound in the presence of an iodide or bromide promoter and heating the resultant reaction mixture under superatmospheric pressures of 500 psi or greater with sufficient carbon monoxide and hydrogen to satisfy the stoichiometry of the desired higher carboxylic acid homologues, until substantial formation of the desired acids containing at least 3 carbon atoms has been achieved, and recovering said desired acids.

It has been found that the homologation reaction is effected only with a synthesis gas mixture, and carbon monoxide alone is not sufficient (contrary to prior art processes involving carbonylation of lower aliphatic alcohols to carboxylic acids).

In addition it has been found here that an iodide or bromide promoter is necessary for acid homologation to take place according to the general scheme outlined above. Lastly, and surprisingly, it has been found that lower alkyl organic iodide or bromide promoters are much more effective than alkali metal iodides or bromides such as cesium iodide.

The following discloses in greater detail the process of invention.

Catalysts that are suitable in the practice of this invention contain ruthenium. The ruthenium-containing catalyst may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise ruthenium in complex combination with carbon monoxide and hydrogen. The most effective catalyst is achieved where the ruthenium hydrocarbonyl species is solubilized in the carboxylic acid co-reactant employed to satisfy the stoichiometry of eq. 1.

The ruthenium catalyst precursors may take many different forms. For instance, the ruthenium may be added to the reaction mixture in an oxide form, as in the case of, for example, ruthenium (IV) oxide hydrate, anhydrous ruthenium (IV) dioxide and ruthenium (VIII) tetraoxide. Alternatively, it may be added as the salt of a mineral acid, as in the case of ruthenium (III) chloride hydrate, ruthenium (III) bromide, ruthenium (III) triiodide, tricarbonyl ruthenium (II) iodide, anhydrous ruthenium (III) chloride and ruthenium nitrate, or as the salt of a suitable organic carboxylic acid, for example, ruthenium (III) acetate, ruthenium (III) propionate, ruthenium butyrate, ruthenium (III) trifluoroacetate, ruthenium octanoate, ruthenium napththenate, ruthenium valerate and ruthenium (III) acetylacetonate. The ruthenium may also be added to the reaction zone as a carbonyl or hydrocarbonyl derivative. Here, suitable examples include triruthenium dodecacarbonyl, hydrocarbonyls such as $H_2Ru_4(CO)_{13}$ and $H_4Ru_4(CO)_{12}$, and substituted carbonyl species such as the tricarbonylruthenium (II) chloride dimer, $[Ru(CO)_3Cl_2]_2$.

Ruthenium complexes containing VB dimer ligands such as triphenylphosphine may be effective catalyst precursors under certain conditions.

Preferred ruthenium-containing compounds include oxides of ruthenium, ruthenium salts of a mineral acid, such as ruthenium iodide salts and ruthenium salts of an organic carboxylic acid and ruthenium carbonyl or hydrocarbonyl derivatives. Among these, particularly preferred are ruthenium (III) triiodide, tricarbonyl ruthenium (II) iodide, ruthenium (IV) dioxide hydrate, ruthenium (VIII) tetraoxide, ruthenium (III) chloride hydrate, ruthenium acetate, ruthenium propionate, ruthenium (III) acetylacetonate, triruthenium dodecacarbonyl and tricarbonyl ruthenium (II) chloride.

The iodide or bromide promoter found necessary to effect the desired acid homologation reaction may be in combined form with the ruthenium, as for instance in ruthenium (III) iodide and $Ru(CO)_3I_2$, but it is generally preferred to have an excess of halogen present in the catalyst system as a promoting agent. By excess is meant an amount of halogen greater than three atoms of halogen per atom of ruthenium in the catalyst system. This promoting component of the catalyst system may consist of a halogen, and/or a halogen compound, that may be introduced into the reaction zone in a gaseous or liquid form, or saturated in a suitable solvent or reactant. Satisfactory halogen promoters include hydrogen halides, such as hydrogen iodide and gaseous hydriodic acid, alkyl and aryl halides containing 1 to 12 carbon atoms such as methyl iodide, ethyl iodide, 1-iodopropane, 2-iodobutane, 1-iodobutane, methyl bromide, ethyl bromide, iodobenzene and benzyl iodide as well as acyl iodides such as acetyl iodide. Also suitable as halogen coreactants are the guaternary ammonium and phosphonium halides; examples include tetramethylammonium iodide and tetrabutylphosphonium iodide. Alkali and alkaline earth halides, such as cesium iodide, may also be used but are generally not as effective as other listed promoters for this homologation.

The lower alkyl iodide or bromide promoters containing 1-6 carbon atoms are the preferred coreactants for the ruthenium-catalyzed acid homologation reaction of this invention. Most preferred are methyl iodide and ethyl iodide.

Starting carboxylic acids useful in the process of this invention are aliphatic acids containing 2-6 carbon atoms. Preferably, said acids are also useful as solvents for the ruthenium catalysts. Suitable carboxylic acids include acetic, propionic, butyric, isobutyric, valeric and caproic, together with dialiphatic acids of 2 to 6 carbon atoms, such as oxalic, malonic, succinic and adipic acids. The invention further contemplates the use of substituted monoaliphatic acids containing one or more functional substitutuents, such as the lower alkoxy, chloro, fluoro, cyano, alkylthio, and amino functional groups, examples of which include acetoacetic acid, dichloroacetic and trifluoroacetic acid, chloropropionic acid, trichloroacetic acid, monofluoroacetic acid and the like. Mixtures of said carboxylic acids, in any ratio, may also be used in the inventive process. The preferred carboxylic acids homologized here are acetic acid and propionic acid, with acetic acid being most preferred.

The quantity of ruthenium catalyst employed in the instant invention is not critical and may vary over a wide range. In general, the novel process is desirably conducted in the presence of a catalytically effective quantity of the active ruthenium species which gives the desired products in reasonable yields. The reaction proceeds when employing as little as about $1 \times 10^{-6}$ weight percent, and even lesser amounts, of ruthenium, based on the total weight of the reaction mixture. The upper concentration is dictated by a variety of factors including catalyst cost, partial pressures of carbon monoxide and hydrogen, operating temperature and choice of carboxylic acid diluent/reactant. A ruthenium catalyst concentration of from about $1 \times 10^{-5}$ to about 10 weight percent ruthenium, based on the total weight of reaction mixture, is generally desirable in the practice of this invention.

The temperature range which can usefully be employed in these syntheses is a variable dependent upon other experimental factors, including the choice of carboxylic acid co-reactant, the pressure, and the concentration and choice of particular species of ruthenium catalyst among other things. The range of operability is from about 100° to 350° C. when superatmospheric pressures of syngas are employed. A narrower range of 180°–250° C. represents the preferred temperature range.

Superatmospheric pressures of 500 psi or greater lead to substantial yields of desirable aliphatic carboxylic acid higher homologues by the process of this invention. A preferred operating range is from 1000 psi to 7500 psi, although pressures above 7500 psi also provide useful yields of desired ester. The pressures referred to here represent the total pressure generated by all the reactants, although they are substantially due to the carbon monoxide and hydrogen fractions in these examples.

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of eq (1).

As far as can be determined, without limiting the invention thereby, the ruthenium-catalyst one-step acid homologation process disclosed herein leads to the formation of acid products primarily containing one carbon atom more than the starting material. Minor amounts of higher acid homologues containing two or three additional carbons are also usually present. In the case then where acetic acid is the co-reactant, the principal products are propionic acid, butyric acid and valeric acid. By-products such as water and ethyl acetate are also detected in the liquid product fraction. Where propionic acid is the reactant acid, the principal products are n-butyric acid and iso-butyric acid. The ratio of isomeric n to iso acids is commonly about 3:1.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired acid product, and said material may be recovered by methods well known in the art, such as distillation, fractionation, extraction and the like. A fraction rich in ruthenium catalyst components may then be recycled to the reaction zone, if desired, and additional products generated.

The products have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts in weight; all temperatures are in degrees centrigrade and all pressures in pounds per square inch gauge (psi).

Having described the inventive process in general terms, the following examples are submitted to supply specific and illustrative embodiments.

EXAMPLE I

To a $N_2$-flushed liquid mix of acetic acid (50 gm) and methyl iodide (5.67 gm., 40 mmole) set in a glass-liner was added 0.763 gm of ruthenium oxide hydrate (53% Ru, 4.0 mmole). The mixture was stirred to partially dissolve the ruthenium, and the glass liner plus contents charged to a 450 ml rocking autoclave. The reactor was flushed with $CO/H_2$, pressured to 4000 psi with $CO/H_2$ (1:1) and heated, with rocking to 220° C. After 18 hrs, the gas uptake was 2400 psi. Upon cooling, depressuring and sampling the off-gas, the clear deep-red liquid product was recovered from the glass-lined reactor. Analysis by glc showed the presence of:

26.9% propionic acid
2.3% isobutyric acid
3.6% n-butyric acid
0.4% iso-valeric acid
0.6% 2-valeric acid
7.72% water
54.1% unreacted acetic acid Typical off-gas samples showed the presence of:
36.7% carbon monoxide
39.3% hydrogen
14.9% carbon dioxide

EXAMPLES 2–9

Following the general procedure of Example 1, additional catalysts and promoters were employed, as well as a different starting aliphatic carboxylic acid. Specifically:

(a) Runs 2 and 7 demonstrate the effective use of ethyl iodide and hydrogen iodide, while tetrabutylphosphonium iodide and ethyl bromide yielded higher MW acids in runs 8 and 9.

(b) Ruthenium (III) chloride, ruthenium (III) acetylacetonate and triruthenium dodecacarbonyl were each successfully employed as soluble catalysts in runs 4, 5 and 6 respectively.

(c) In Run 3 propionic acid was homologized yielding an n-butyric acid in a total weight percent concentration of 18.2% with only 1.5 weight percent acetic acid (a lower homologue) being produced.

Results are summarized in Table I below:

TABLE 1[a,b]

| | | | | PRODUCT LIQUID COMPOSITION CONC. (wt %[c]) | | | | | | | |
|---|---|---|---|---|---|---|---|---|---|---|---|
| | | | Aliphatic | | | | HOBu | | HOVa | | |
| Run | Catalyst | Promoter | Acid | $H_2O$ | HOAc | HOPr | Iso | n | iso | n | EtOAc |
| 1 | $RuO_2$ | - 10 MeI | HOAc | 7.7 | 54.1 | 26.9 | 2.3 | 3.6 | 0.4 | 0.6 | 1.5 |
| 2 | $RuO_2$ | - 10 EtI | HOAc | 24.5 | 46.1 | 19.3 | 0.7 | 1.3 | 2.6 | 0.5 | |
| 3 | $RuO_2$ | - 10 MeI | HOPr | 17.6 | 1.5 | 48.6 | 5.4 | 12.8 | 1.5 | 1.6 | |
| 4 | $RuCl_3$ | - 10 MeI | HOAc | 25.8 | 27.2 | 17.4 | 1.5 | 3.9 | | 0.2 | 7.7 |
| 5 | $Ru(ACAC)_3$ | - 10 MeI | HOAc | 30.1 | 29.4 | 17.6 | 0.6 | 5.5 | | | 1.6 |
| 6 | $Ru_3(CO)_{12}$ | - 10 MeI | HOAc | 25.0 | 24.6 | 17.6 | 1.0 | 5.1 | 2.6 | 0.7 | 2.0 |
| 7 | $RuO_2$ | - 10HI[d] | HOPr | | | 48.6 | 3.2 | 12.8 | | 1.2 | |
| 8 | $RuO_2$ | - $Bu_4PI$ | HOAc | 0.1 | 87.4 | 5.9 | 1.8 | | | | |
| 9 | $RuO_2$ | - 10 EtBr | HOAc | 17.6 | 8.6 | 19.5[e] | | | | | |

[a]Run Charge: Aliphatic Acid, 50 gm; Iodide Promoter, 40 mmole; Ruthenium catalyst, 4.0 mmole.
[b]Run Conditions: Initial pressure 4000 psi of $CO/H_2$ (1:1), 220° C., 18 hr.
[c]Designations: Propionic acid, HOPr; Butyric Acid, HOBu; and Valeric acid, HOVa.
[d]Injected into the reactor as gaseous hydrogen iodide
[e]A two-phase liquid product, low liquid yield, major fractions are methyl acetate (21%) and ethanol (19%)

EXAMPLES 10–18

In these examples, the general procedures of Example 1 are followed, and the ruthenium oxide, methyl iodide combination is employed to catalyze acetic acid homologation. However, propionic and $C_3$+acid syntheses are effected over a range of different temperatures, pressures, ruthenium catalyst concentrations and Ru/I mole ratio.

Results are summarized in Table II, below:

TABLE II[a]

| | Charge | (mmole) | HOAc | Initial Pressure | Operating Temp | PRODUCT LIQUID COMPOSITION CONC. (wt %) | | | | | |
|---|---|---|---|---|---|---|---|---|---|---|---|
| | | | | | | | | | HOBu | | |
| Run | $RuO_2$ | MeI | (gm) | (psi) | (°C.) | $H_2O$ | HOAc | HOPr | iso | n | EtOAc |
| 10 | 2.0 | 20 | 25 | 2000 | 220 | 19.9 | 38.2 | 13.4 | 0.1 | | 14.4 |
| 11 | 4.0 | 40 | 50 | 4000 | 250 | 46.8 | 32.0 | 13.7 | 1.6 | 3.1 | |

TABLE II[a]-continued

| Run | Charge RuO$_2$ | (mmole) MeI | HOAc (gm) | Initial Pressure (psi) | Operating Temp (°C.) | PRODUCT LIQUID COMPOSITION CONC. (wt %) | | | | | |
|---|---|---|---|---|---|---|---|---|---|---|---|
| | | | | | | H$_2$O | HOAc | HOPr | HOBu iso | n | EtOAc |
| 12 | 4.0 | 40 | 15 | 4000 | 180 | 13.8 | 41.5 | 4.8 | 0.4 | | 24.8 |
| 13 | 4.0 | 40 | 15 | 1000 | 220 | 7.1 | 74.0 | 6.5 | 0.1 | 0.1 | 2.2 |
| 14 | 4.0 | 80 | 50 | 4000 | 220 | 25.0 | 34.1 | 16.0 | 2.3 | 2.6 | |
| 15 | 2.0 | 40 | 50 | 4000 | 220 | 24.2 | 31.9 | 15.9 | 0.5 | 4.5 | |
| 16 | 0.5 | 40 | 50 | 4000 | 220 | 13.0 | 57.1 | 4.3 | | 0.6 | 14.0 |
| 17 | 8.0 | 10 | 50 | 4000 | 220 | 6.5 | 52.4 | 0.6 | 0.8 | | 19.4 |
| 18 | 16.0 | 160 | 50 | 4000 | 220 | 33.6 | 18.8[b] | 16.8 | 1.7 | 1.5 | 3.3 |

[a]Run Conditions and Product Designations as per TABLE 1.
[b]Two-phase liquid product, the 4–5 ml of 'Light' Phase contains 23.5% propionic acid, 13.4% butyric acids, 8.9% valeric acids plus 0.1% mexanose acid.

EXAMPLE 19

To a N$_2$-flushed liquid mix of acetic acid (50 gm) and methyl iodide (5.67 gm, 40 mmole) set in a glass-liner was added 0.763 gm of ruthenium oxide, hydrate (53% Ru, 4.0 mmole). The mixture was stirred to partially dissolve the ruthenium, and the glass liner plus contents charged to a 800 ml working autoclave. The reactor was flushed with CO/H$_2$, pressured to 2000 psi with CO/H$_2$ (1:1) and heated to 220° C. Additional CO/H$_2$ was then introduced from a large surge tank into the reactor and the total pressure in the reactor raised to 6300 psi. The pressure was held at 6000–6300 psi throughout the 18 hr. run by incremental additional of CO/H$_2$ from the surge tank.

After cooling the reactor, sampling the off-gas and depressuring, 63.2 gm of clear yellow-red liquid was recovered from the glass-lined reactor. There was no solid phase. Analyses of the liquid phase by glc shows the presence of:
18.2 wt% propionic acid
6.4 wt% n-butyric acid
0.6 wt% iso-butyric acid
1.0 wt% n-valeric acid
25.4 wt% water
26.4 wt% unreacted acetic acid Typical off-gas samples showed the presence of:
24.2% hydrogen
42.5% carbon monoxide
13.9% carbon dioxide
2.3% methane Finally, the invention is advantageous in that numerous substitutions, modifications and changes can be made without departing from the inventive concept. However, the scope of the subject invention may best be understood by examining the claims, which follow, read in conjunction with the preceding specification.

What is claimed is:

1. A process of preparing higher homologues of aliphatic carboxylic acids containing 2–6 carbon atoms which comprises the steps of contacting said aliphatic acid starting material with at least a catalytic amount of a ruthenium-containing compound in the presence of an iodide or bromide promoter and heating the resultant reaction mixture at 100°–350° C. under superatmospheric pressures of 500 psi or greater with sufficient carbon monoxide and hydrogen to satisfy the stoichiometry of the desired higher carboxylic acid homologues, until substantial formation of the desired acids containing at least 3 carbon atoms has been achieved, and recovering said desired acids.

2. The process of claim 1 wherein the ruthenium-containing compound is selected from the group consisting of one or more oxides of ruthenium, ruthenium salts of a mineral acid, ruthenium salts of an organic carboxylic acid and ruthenium carbonyl or hydrocarbonyl derivatives.

3. The process of claim 1 wherein the ruthenium-containing compound is selected from the group consisting of ruthenium (III) triiodide, tricarbonylruthenium (II) iodide, ruthenium (IV) dioxide hydrate, ruthenium (VIII) tetraoxide, ruthenium (III) chloride hydrate, ruthenium acetate, ruthenium propionate, ruthenium (III) acetylacetonate, triruthenium dodecarbonyl and tricarbonylruthenium (II) chloride.

4. The process of claim 1 wherein said iodide or bromide promoter is an alkyl iodide or bromide containing 1–6 carbon atoms.

5. The process of claim 4 wherein said promoter is selected from the group consisting of methyl iodide, methyl bromide, ethyl iodide and ethyl bromide.

6. The method of claim 1 wherein said aliphatic carboxylic acid starting material is acetic acid.

7. The process of claim 1 wherein said ruthenium-containing catalyst is ruthenium (IV) dioxide.

8. The process of claim 1 wherein said ruthenium-containing catalyst is ruthenium (III) trichloride.

9. The process of claim 1 wherein said iodide or bromide promoter is a quaternary ammonium or phosphonium iodide or bromide salt.

10. The process of claim 1 wherein said iodide or bromide promoter is a hydrogen halide.

* * * * *